(12) United States Patent
Kreuzer

(10) Patent No.: US 10,478,123 B2
(45) Date of Patent: Nov. 19, 2019

(54) ELASTIC SENSOR FOR MEASURING VITAL PARAMETERS IN THE AUDITORY CANAL

(71) Applicant: Cosinuss GmbH, Munich (DE)

(72) Inventor: Johannes Kreuzer, Munich (DE)

(73) Assignee: Cosinuss GmbH, Munich (DE)

( * ) Notice: Subject to any disclaimer, the term of this patent is extended or adjusted under 35 U.S.C. 154(b) by 461 days.

(21) Appl. No.: 15/033,774

(22) PCT Filed: Oct. 26, 2014

(86) PCT No.: PCT/EP2014/072929
§ 371 (c)(1),
(2) Date: May 2, 2016

(87) PCT Pub. No.: WO2015/062999
PCT Pub. Date: May 7, 2015

(65) Prior Publication Data
US 2016/0262696 A1 Sep. 15, 2016

(30) Foreign Application Priority Data

Oct. 30, 2013 (DE) .......................... 10 2013 222 131

(51) Int. Cl.
*A61B 5/00* (2006.01)
*A61B 5/08* (2006.01)
(Continued)

(52) U.S. Cl.
CPC .............. *A61B 5/6817* (2013.01); *A61B 5/01* (2013.01); *A61B 5/02055* (2013.01);
(Continued)

(58) Field of Classification Search
CPC ..... A61B 5/6817; A61B 5/01; A61B 5/02055; A61B 5/02416; A61B 5/02438;
(Continued)

(56) References Cited

U.S. PATENT DOCUMENTS 3,796,841 A * 3/1974 Gorman ............... H04R 1/1066
379/430
5,213,099 A 5/1993 Tripp, Jr.
(Continued)

FOREIGN PATENT DOCUMENTS

| DE | 19831361 A1 | 1/1999 |
|---|---|---|
| DE | 102007046295 A1 | 4/2009 |
| EP | 1922989 A2 | 5/2008 |

OTHER PUBLICATIONS

Alexandar et al., Anthropometry of the Human Ear, Aerospace Medical Research Laboratories, USAF, pp. 1-31, Jan. 1968.*
(Continued)

*Primary Examiner* — Eric F Winakur
(74) *Attorney, Agent, or Firm* — Altman & Martin; Steven K Martin

(57) ABSTRACT

A sensor for measuring a vital parameter in the auditory canal comprising a sensor element (1) and a positioning element (3), both connected to a sensor element attachment (2). The positioning element (3) has a shape that reproduces the inside of the ear and positions the sensor element (1) and sensor element attachment (2) at least partially in the auditory canal (8) in a stable manner. The position of the sensor element (1) in the auditory canal (8) is determined by the depth of penetration of the sensor element attachment (2) in the auditory canal (8). The sensor element (1), the sensor element attachment (2), and the positioning element (3) are arranged at least partially in a housing (4) adapted to the anatomy of the person's head.

9 Claims, 1 Drawing Sheet

(51) Int. Cl.
*A61B 5/042* (2006.01)
*A61B 5/1455* (2006.01)
*A61B 5/02* (2006.01)
*A61B 5/0205* (2006.01)
*A61B 5/024* (2006.01)
*A61B 5/01* (2006.01)

(52) U.S. Cl.
CPC ...... *A61B 5/02416* (2013.01); *A61B 5/02438* (2013.01); *A61B 5/042* (2013.01); *A61B 5/0816* (2013.01); *A61B 5/14551* (2013.01); *A61B 5/14552* (2013.01); *A61B 5/6834* (2013.01); *A61B 5/0002* (2013.01); *A61B 2562/164* (2013.01)

(58) Field of Classification Search
CPC ... A61B 5/042; A61B 5/0816; A61B 5/14551; A61B 5/14552; A61B 5/6834
See application file for complete search history.

(56) References Cited

U.S. PATENT DOCUMENTS

| | | | |
|---|---|---|---|
| 6,080,110 A * | 6/2000 | Thorgersen | A61B 5/222 600/322 |
| 6,253,871 B1 | 7/2001 | Aceti | |
| 6,371,639 B1 * | 4/2002 | Huang | A61B 5/01 264/161 |
| 6,427,018 B1 * | 7/2002 | Keliiliki | H04R 1/1066 381/370 |
| 6,556,852 B1 | 4/2003 | Schulze et al. | |
| 9,031,275 B2 * | 5/2015 | Brodsgaard | H04R 1/105 381/370 |
| 2005/0049471 A1 * | 3/2005 | Aceti | A61B 5/14552 600/340 |
| 2005/0059870 A1 * | 3/2005 | Aceti | A61B 5/0002 600/340 |
| 2009/0088611 A1 | 4/2009 | Buschmann | |
| 2009/0221888 A1 | 9/2009 | Wijesiriwardana | |
| 2010/0191144 A1 | 7/2010 | Zoth et al. | |
| 2010/0228315 A1 | 9/2010 | Nielsen | |
| 2010/0331631 A1 * | 12/2010 | MacLaughlin | A61B 5/14552 600/301 |
| 2013/0046159 A1 * | 2/2013 | McCombie | A61B 5/14552 600/324 |
| 2013/0131519 A1 * | 5/2013 | LeBoeuf | A61B 5/0077 600/476 |
| 2014/0187885 A1 | 7/2014 | Kreuzer | |

OTHER PUBLICATIONS

Johaness P. Buschmann and Jin Huang, New Ear Sensor for Mobile, Continuous and Long Term Pulse Oximetry, 32nd Annual International Conference of the IEEE EMBS, Buenos Aires, Argentina, Aug. 31-Sep. 4, 2010, pp. 5780-5783.

Johaness P. Buschmann and Jin Huang, Pulse Oximetry in the External Auditory Canal—a New Method of Mobile Vital Monitoring, IEEE Sensors Journal, vol. 12, No. 3, Mar. 2012, pp. 671-676.

\* cited by examiner

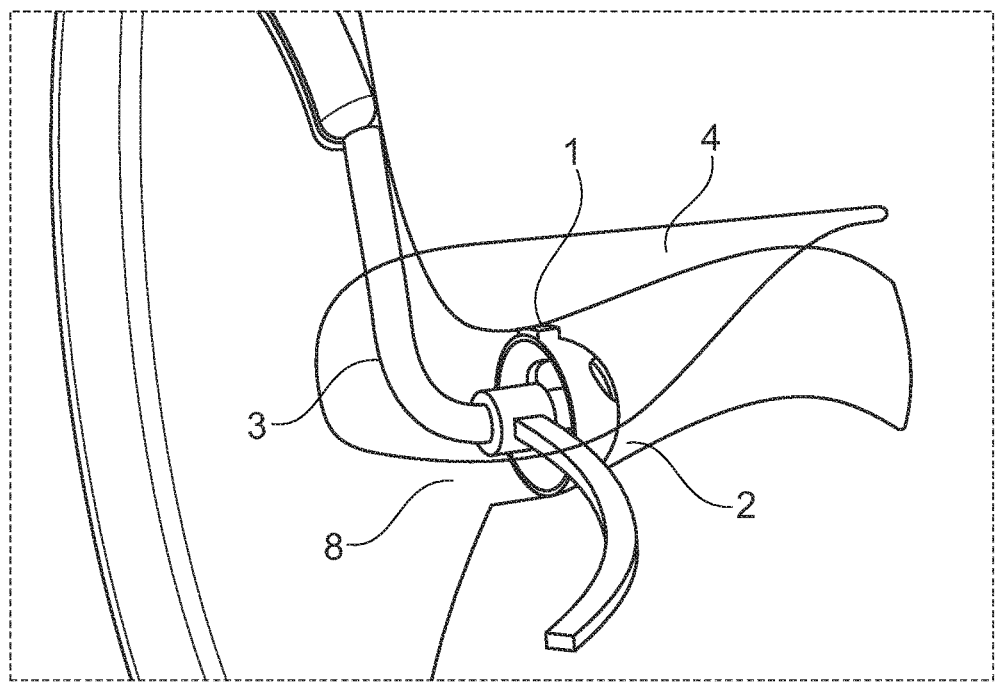

ELASTIC SENSOR FOR MEASURING VITAL PARAMETERS IN THE AUDITORY CANAL

For the measurement of vital parameters such as temperature, pulse rate or oxygen saturation in the auditory canal of a person or an animal, an auditory canal sensor is suitable. Such sensors are used in a predetermined direction, that is, a sensor for the right ear may be worn just on the right and a sensor for the left ear may be worn just on the left. Good measurement results may be achieved only if a stable positioning of the sensor is ensured at the ear or in the ear. In optical measuring methods, for example in pulse oximetry or pulse rate measurement, excellent positioning is required, which either does not change or merely slightly changes when wearing the sensor.

The sensor element fixture usually is opaque. It is known that light emitters and light sensors are mounted on the sensor element fixture as far apart as possible, preferably offset by 180°. Therefore, black sensor element fixtures made of silicone are used commonly. It is known that a black sensor element fixture having a light emitter and light receiver offset by 180° provides for a high modulation depth.

During optical detection of either pulse rate or arterial oxygen saturation using pulse oximetry, light passes through a tissue. This light is modulated by the arterial blood such that pulse rate and oxygen saturation, respectively, may be deduced therefrom.

The arrangement of individual sensor elements is not trivial in order to measure simultaneously temperature and other parameters by means of optical components. Light emitters not only pass light through the tissue, but also generate heat via current flow. This heat may not exceed a defined loss of dissipation in order for the user to be unaware of a warming. Moreover, the warming may not distort a concurrent temperature measurement.

It is the object of the invention to provide for a sensor capable of not limiting the user's mobility, which is comfortable to wear, which ensures an optimum fit and which is adaptable to suit different anatomical conditions. Furthermore, the sensor should be adaptable to either ear of a person or an animal and provide for a high quality signal at high modulation depth.

This object is achieved in that a sensor is provided for measuring a vital parameter in the auditory canal of a person or an animal, wherein the sensor comprises a sensor element fixture, which may be positioned at least partially in the auditory canal, a sensor element, which is connectable to the sensor element fixture and may be positioned at least partially in auditory canal, and a positioning element adapted to position the sensor element fixture within the auditory canal, wherein at least one end of the positioning element may be connected to the sensor element fixture, and wherein the position of the sensor element in the auditory canal is determined by the insertion depth of the sensor element fixture in the auditory canal, and wherein the positioning element is characterized by a suitable shape relating to the anatomy of the interior face of the auricle, and is suitable for pushing the sensor element fixture into the interior of the auditory canal, such that the sensor is held firmly and a continuous measurement of the vital parameter is carried out in the auditory canal, wherein the sensor element, the sensor element fixture and the positioning element are arranged at least partially in a housing and wherein the housing is adaptable to the anatomy of at least part of the head of the person or the animal.

Preferably, the external auditory canal is used as a measuring site, which is particularly suitable for mobile or continuous sensor technology, respectively, due to the combination of physiological properties on the one hand and mechanical, technical and/or functional features on the other hand. The term "measuring a vital parameter" relates to the measuring of at least one, i.e. also two or more parameters, which may be measured simultaneously. The expression relating to the connectability of the sensor element and the sensor element fixture denotes that the sensor element may be connected to the sensor element fixture in particular via further components of the sensor or via lines, wires, cables or the like. The sensor element may also contact the sensor element fixture directly, i.e. it may be mounted directly to the sensor element fixture. Preferably, the sensor element fixture comprises the sensor element, i.e. the sensor element is formed as a part of the sensor element fixture. The feature that the position of the sensor element in the auditory canal is determined by the insertion depth of the sensor element fixture in the auditory canal, denotes that the positioning of the sensor element carried out relative to the sensor element fixture enabling a precise and continuous measurement of the vital parameter, in particular, sensor element and sensor element attachment positioned close to each other in order for proper signal transmission between the sensor element fixture and the sensor element. Preferably, positioning element and sensor element fixture are formed integrally.

The term "sensor element" denotes the sensor, i.e. the actual sensor, which converts the actual physiological or biological variable into an electrical signal, such as a converter, a semiconductor, a probe or electrodes. The terms "sensor element fixture" and "positioning element and" denote devices, connected operatively in a functional and/or mechanical manner, which, in combination, position the sensor element relative to the wall of the auditory canal such that the physiological and biological parameters may be measured with as low interference as possible. It is the task of the sensor element fixture to define the radial position of the sensor element, while it is for the positioning element to define the axial position. According to other preferred embodiments of the invention both functions are not separable or they merge together. In particular, the term "sensor" denotes the combination of the sensor element, the sensor element fixture and positioning element. According to other preferred embodiments of the invention, the term "sensor" also refers to the evaluation unit, which is preferably located behind the ear and is adapted to provide support for the sensor.

Preferably, the vital parameter comprises at least one physiological, biochemical and/or bioelectrical parameter, in particular, the vital parameter is selected from the group comprising body temperature, blood oxygen saturation, heart rate, an electrical parameter of the heart, respiratory rate, concentration of substances dissolved in blood, in particular the arterial oxygen saturation, concentration of substances present in tissue, physical activity and the body position.

Thus, the sensor element, the sensor element fixture and the positioning element according to the invention are at least partially disposed in a housing and the housing is adaptable to the anatomy of at least a portion of the head of the person or the animal. The adaptability of the housing is preferably predetermined by the elasticity of at least a part of the housing and/or the sensor. Thus, the user is not hampered or disturbed regarding his/her mobility, the sensor may be worn comfortably, and does ensure an optimal fit. Furthermore, the sensor is adaptable to various anatomical conditions; in particular, it is adaptable to both ears of a person or an animal.

The term "mobility" not only refers to mobility but also to a wireless transmission of the data collected, for example via radio. Common wireless protocols such as Bluetooth or ZigBee are either working in the 2.4 to 2.5 GHz bands reserved worldwide or in the ISM band, that is, at 868 MHz in Europe and at 912 MHz in the US.

The sensor of the invention is adaptable, preferably anatomically adaptable, and preferably has a flexible part connecting two rigid parts and thus at least partially conforms to the anatomy of the head of the person or the animal. This includes the distance of the auricle in the upper portion of the head (where the auricle is positioned on the head), to the auditory canal, as well as the angular range in between the two. Due to the flexible or resilient part, applying the sensor is more pleasant or placing of the sensor on the head is made possible thereby, respectively.

According to a preferred embodiment of the invention, the housing is at least partially elastic; it is particularly preferred when the housing is rotatable and/or adjustable in size. The term "rotate" indicates that the housing, when viewed from the head of the person or the animal, may be twisted or adjusted, respectively, to the left or right as to be adaptable to the anatomical conditions. The elasticity of the flexible part ensures optimum grip and thus has a defined restoring force. Due to the elasticity, the sensor is held firmly at the auricle. Preferably, rotation is not achieved via the elastic housing, but via a piston guide.

According to a further preferred embodiment of the invention, the housing comprises a piston and a guide, wherein the piston is at least partially aligned in the guide. The piston, extending at least partially in the guide, ensures the size adjustment. Furthermore, the length of the positioning element may be adapted or adjusted, respectively, to any size reflecting the distance between the auricle in the upper portion of the head and the center of the entrance of the auditory canal. The piston and its guide are arranged preferably such that they may be pulled apart easily in the 0° position, i.e. they are size-adjustable, and such that a rotation of up to −120° or +120° results in a deadlock, in which case no size adjustment is possible. The shape of the piston and its guide ensures that a rotation by more than +120° or −120° is impossible. Here, the 0° position is anatomically the direction forward or backward, viewed from the head of the person or the animal. By rotating in a "positive" direction, from a head's perspective, the sensor thus may be adapted to one side of the head, by rotating in a "negative" direction, to the other side. Advantageously, the deadlock of piston and guide is achieved due to a resilient and a rigid material. Thus, by the deformation of the elastic piston a predefined force is produced, such that size adjustment and adaptation of direction does not occur during normal use. Preferably, the piston and/or the guide are arranged with a material comprising a plastic, a rubber, a silicone and/or an elastomer. Preferably, the material of the solid component comprises plastic and the material of the flexible component comprises at least one of rubber, silicone and elastomer. Advantageously, both materials withstand severe weather conditions such as salt water, cold, sunlight, as well as contact with skin, sweat etc. Preferably, the flexible or elastic part exhibits low abrasion. According to other preferred embodiments the piston comprises a rigid or non-elastic material, and the guide comprises a resilient material.

In another preferred embodiment of the invention, the housing defines the length of the positioning element, a length of the positioning element of 10 mm and/or 50 mm is particularly preferred. This results in an optimal adaptation of the positioning element in case of its being used by a person. The length of the positioning element may differ with respect to this range of lengths when utilized in an animal, without thereby departing from the inventive concept of the invention.

According to another preferred embodiment of the invention, the sensor element fixture may be arranged to be insertable and/or replaceable. Thus, the sensor element fixture is easily replaceable and adaptable, which is particularly advantageous since the diameter of the auditory canal may vary in different people or animals. The sensor element fixture preferably is present in different sizes. For connecting the sensor element, advantageously both, a mechanical connection and an electrical connection, are provided.

In another preferred embodiment of the invention, the sensor element fixture is at least partially white. Usually, a white sensor element fixture is partially translucent at wavelengths of 400 nm to 1000 nm, by an arrangement of the optical components, however, twisted by 90°, shunt light is effectively prevented, providing for excellent measurement with high modulation depths. This allows for obtaining good signal quality, since the depth of modulation is increased, equalling a high signal-to-noise ratio. Thus, the sensor according to the invention achieves a good signal quality at high or optimal depth of modulation. With simultaneous measurement of temperature and pulse rate or with pulse oximetry, the inventive arrangement comprises the different sensor elements, wherein the sensor element which measures temperature is placed further within the auditory canal, and the optical sensor elements are placed further out at the entrance of the auditory canal. Furthermore, it is important in the arrangement to ascertain that the temperature sensor and the light emitter or the light emitters are arranged as far away from each other as possible, as to avoid problems of temperature measurement caused by the power dissipation of the light emitter. The greatest possible distance is constituted by a 180° rotation of the temperature sensor with respect to the light emitter and by an offset, i.e. the temperature sensor being further inside and the light emitter being further outside.

According to a further preferred embodiment of the invention, a protective cap is provided which may be placed onto the sensor element fixture. Preferably, the cap is translucent in the wavelength range of 400 nm and/or 1000 nm and/or is provided with a thickness of material of 0.005 mm and/or 1 mm. Regarding hygiene requirements, the cap is particularly advantageous when it is pulled at least partially over the sensor element fixture. Advantageously, the protective cap may be provided for single use. The protective cap is preferably thin and comprises a flexible material in order to avoid interfering with the measurement.

In another preferred embodiment of the invention, an antenna is provided, which is capable of being incorporated, at least partially, within the sensor, particularly preferably within the positioning element. It is particularly preferred when the antenna is fully incorporated within the sensor, such that the assembly remains compact. For regular data transfers, suitable antennas having a suitable length are required. Here, the length of the antenna is indirectly proportional to the radio frequency used. At 868 MHz, a regular λ/4-antenna is about 8.6 mm long. Advantageously, this length is housed in the sensor without increasing the size of the sensor. Particularly preferably, the antenna is at least partially incorporated within the positioning member.

In the following, the invention based on a preferred embodiment will be explained further in detail with reference to the drawing.

FIG. 1 shows a sensor according to a first preferred embodiment of the invention.

FIG. 1 shows a sensor according to a first preferred embodiment of the invention. It is apparent from FIG. 1 that the positioning element 3, the sensor element 1 and the sensor element fixture 2 are arranged in a housing 4 and that the housing 4 is adaptable to the anatomy of the head of a person. The sensor element fixture 2 has a white color. This opacity is not essential. The light path is extended by reflection. In order to achieve an optimal positioning between energy and measuring signal and to prevent constructively shunt light, positioning at 90° is required. The housing 4 is formed partly rigid and partly flexible. According to this preferred embodiment, the housing 4 is configured to be rotatable and adjustable in size. Furthermore, the sensor element fixture 2 is configured to be replaceable.

According to other preferred embodiments of the invention, sensor element fixtures are provided having differently colored silicone shields. Thereby, the intensity level of the white color of the sensor element fixtures influences the quality of the signal. The present inventors have discovered that the whiter the sensor element fixture, the better the signal quality.

The invention claimed is:

1. A sensor for measuring a vital parameter in the auditory canal (8) of a person or an animal, comprising:
    a sensor element fixture (2), which is positionable at least partially in the auditory canal (8),
    a sensor element (1), which is connectable to the sensor element fixture (2) and is positionable at least partially in the auditory canal (8), and
    a positioning element (3), suitable for positioning the sensor element fixture (2) in the auditory canal (8), wherein at least one end of the positioning element (3) is connectable to the sensor element fixture (2),
    wherein the position of the sensor element (1) within the auditory canal (8) is determined by the insertion depth of the sensor element fixture (2) in the auditory canal (8), and
    wherein the positioning element (3) exhibits a suitable shape relating to the anatomy of the interior face of the auricle, and is suitable for pushing the sensor element fixture (2) into the interior of the auditory canal such that the sensor is held firmly and a continuous measurement of the vital parameter occurs in the auditory canal (8) characterized in that
    the sensor element (1), the sensor element fixture (2) and the positioning element (3) are arranged at least partially in a housing (4) and the housing (4) is adaptable to the anatomy of at least part of the head of the person or the animal, wherein the housing (4) is at least partially elastic, the housing (4) is rotatable and/or size adjustable, the housing (4) comprises a piston and a guide wherein the piston is at least partially aligned in the guide, the piston and/or the guide are arranged with a material comprising a plastic, a rubber, a silicone and/or an elastomer such that they may be pulled apart in the 0° position and such that a rotation of up to −120° or +120° results in a deadlock, wherein the 0° position lies in a plane parallel to the sagittal plane of the head.

2. The sensor according to claim 1, wherein the housing (4) defines the length of the positioning element (3) and the length of the positioning element (3) is ≥10 mm and/or ≤50 mm.

3. The sensor according to claim 1, wherein the sensor element fixture (2) is arranged to be insertable and/or replaceable.

4. The sensor according to claim 1 wherein the sensor element fixture (2) is at least partially white.

5. The sensor according to claim 1, wherein a protective cap is provided which may be placed onto the sensor element fixture (2).

6. The sensor according to claim 5, wherein the protective cap is translucent in the wavelength range of ≥400 nm and/or ≤1000 nm and/or is provided with a thickness of material of ≥0.005 mm and/or ≤1 mm.

7. The sensor according to claim 1, wherein an antenna is provided which is capable of being incorporated, at least partially, within the sensor.

8. The sensor according to claim 7, wherein the antenna is at least partially within the positioning element (3).

9. The sensor according to claim 1, wherein the deadlock of piston and guide is achieved due to a resilient and a rigid material.

* * * * *